US00PP32203P3

(12) United States Plant Patent
Post

(10) Patent No.: US PP32,203 P3
(45) Date of Patent: Sep. 15, 2020

(54) ***CHRYSANTHEMUM* PLANT NAMED 'DLFBAV1'**

(50) Latin Name: ***Chrysanthemum* X *morifolium***
Varietal Denomination: DLFBAV1

(71) Applicant: Arie Gerard Post, Delft (NL)

(72) Inventor: Arie Gerard Post, Delft (NL)

(73) Assignee: Deliflor Royalties B.V., Maasdijk (NL)

( * ) Notice: Subject to any disclaimer, the term of this patent is extended or adjusted under 35 U.S.C. 154(b) by 0 days.

(21) Appl. No.: 16/602,044

(22) Filed: Jul. 25, 2019

(65) Prior Publication Data

US 2020/0053932 P1 Feb. 13, 2020

Related U.S. Application Data

(60) Provisional application No. 62/764,554, filed on Aug. 7, 2018.

(51) Int. Cl.
*A01H 5/02* (2018.01)
*A01H 6/14* (2018.01)

(52) U.S. Cl.
USPC ..... Plt./288
CPC ..... *A01H 6/1424* (2018.05)

(58) Field of Classification Search
USPC ..... Plt./263.1, 284, 286, 287, 288
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Chrysanthemum* plant named 'DLFBAV1', characterized by its upright plant habit; vigorous growth habit; dark green-colored leaves; uniform flowering habit; strong upright flowering stems typically grown as a disbud-type with one inflorescence per lateral branch; large decorative-type inflorescences with white-colored ray florets; excellent postproduction longevity; and tolerance to low and high temperatures.

2 Drawing Sheets

Botanical designation: *Chrysanthemum* X *morifolium*.
Cultivar denomination: 'DLFBAV1'.

CROSS-REFERENCED TO CLOSELY RELATED APPLICATIONS

Title: Varieties of *Chrysanthemum* Plants
Applicant: Arie Gerard Post
Provisional application Ser. No. 62/764,554
Filed: Aug. 7, 2018

BACKGROUND OF THE INVENTION

The present invention relates to a new and distinct cultivar of *Chrysanthemum* plant, botanically known as *Chrysanthemum* X *morifolium*, commercially grown as a cut flower and hereinafter referred to by the name 'DLFBAV1'.

The new *Chrysanthemum* plant is a product of a planned breeding program conducted by the Inventor in Maasdijk, The Netherlands. The objective of the breeding program is to create new cut *Chrysanthemum* plants with attractive inflorescences, strong flowering stems and excellent post-production longevity.

The new *Chrysanthemum* plant is a naturally-occurring whole plant mutation of *Chrysanthemum* x *morifolium* 'DLFBAV3', not patented. The new *Chrysanthemum* plant was discovered and selected as a single flowering plant from within a population of plants of 'DLFBAV3' in a controlled greenhouse environment in Maasdijk, The Netherlands on Feb. 13, 2017.

Asexual reproduction of the new *Chrysanthemum* plant by vegetative terminal cuttings since Feb. 13, 2017 has shown that the unique features of this new *Chrysanthemum* plant are stable and reproduced true to type in successive generations of asexual reproduction.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'DLFBAV1'. These characteristics in combination distinguish 'DLFBAV1' as a new and distinct *Chrysanthemum* plant:

1. Upright plant habit; vigorous growth habit.
2. Dark green-colored leaves.
3. Uniform flowering habit.
4. Strong upright flowering stems typically grown as a disbud-type with one inflorescence per lateral branch.
5. Large decorative-type inflorescences with white-colored ray florets.
6. Excellent postproduction longevity.
7. Relatively tolerant to low and high temperatures.

Plants of the new *Chrysanthemum* differ primarily from plants of the mutation parent, 'DLFBAV3', in ray floret color as plants of the new *Chrysanthemum* have white-colored ray florets whereas plants of 'DLFBAV3' are light purple in color.

Plants of the new *Chrysanthemum* can be compared to plants of *Chrysanthemum* X *morifolium* 'Zembla', disclosed in U.S. Plant Pat. No. 14,052. In side-by-side comparisons plants of the new *Chrysanthemum* differ primarily from plants of 'Zembla' in the following characteristics:

1. Inflorescences of plants of the new *Chrysanthemum* are denser than inflorescences of plants of 'Zembla'.
2. Ray florets of plants of the new *Chrysanthemum* are slightly whiter in color than ray florets of plants of 'Zembla'.

Plants of the new *Chrysanthemum* can also be compared to plants of *Chrysanthemum* X *morifolium* 'DLFGAGA1', not patented. In side-by-side comparisons plants of the new *Chrysanthemum* differ primarily from plants of 'DLFGAGA1' in the following characteristics:

1. Plants of the new *Chrysanthemum* have smaller in inflorescences than plants of 'DLFGAGA1'.
2. Ray florets of plants of the new *Chrysanthemum* are slightly whiter in color than ray florets of plants of 'DLFGAGA1'.

BRIEF DESCRIPTION OF THE PHOTOGRAPHS

The accompanying colored photographs illustrate the overall appearance of the new *Chrysanthemum* plant showing the colors as true as it is reasonably possible to obtain in colored reproductions of this type. Colors in the photographs may differ slightly from the color values cited in the detailed botanical description which accurately describe the colors of the new *Chrysanthemum* plant.

The photograph on the first sheet comprises a side perspective view of a typical flowering stem of 'DLFBAV1' grown as a disbud-type.

The photograph on the second sheet comprises close-up views of the lower (top of the photographic sheet) and upper surfaces (bottom of the photographic sheet) of typical inflorescences and leaves of 'DLFBAV1'.

DETAILED BOTANICAL DESCRIPTION

The aforementioned photographs and following observations and measurements describe plants grown during the spring in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 22° C., night temperatures ranged from 20° C. to 25° C. and light levels averaged 8 klux. Plants were grown as single-stem disbud-type plants and were ten weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFBAV1'.

Parentage: Naturally-occurring whole plant mutation of *Chrysanthemum* x *morifolium* 'DLFBAV3', not patented.

Propagation:

*Type*.—Terminal vegetative cuttings.

*Time to initiate roots, summer*.—About six days at temperatures about 24° C.

*Time to initiate roots, winter*.—About eight days at temperatures about 22° C.

*Time to produce a rooted young plant, summer*.—About twelve days at temperatures about 24° C.

*Time to produce a rooted young plant, winter*.—About two weeks at temperatures about 22° C.

*Root description*.—Fine, fibrous; typically creamy white in color, actual color of the roots is dependent on substrate composition, water quality, fertilizers, substrate temperature and physiological age of roots.

*Rooting habit*.—Freely branching, medium density.

Plant description:

*Plant and growth habit*.—Herbaceous decorative-type cut flower that is typically grown as a single stem disbud-type; upright plant habit; vigorous growth habit and moderate to rapid growth rate.

*Plant height, soil level to top of foliar plane*.—About 95.6 cm.

*Plant height, soil level to top of inflorescence plane*.—About 102.7 cm.

*Plant diameter (foliar)*.—About 19.2 cm.

*Plant diameter (floral)*.—About 11.3 cm.

*Flowering stem length*.—About 98.3 cm.

*Flowering stem diameter*.—About 8 mm.

*Flowering stem internode length*.—About 2.8 cm.

*Flowering stem strength*.—Strong.

*Flowering stem aspect*.—Erect.

*Flowering stem texture and luster*.—Moderately pubescent; slightly glossy.

*Flowering stem color, developing*.—Close to 144A, at the internodes, close to 146B.

*Flowering stem color, developed*.—Close to 144A and 146B.

*Leaf description*.—Arrangement: Alternate; simple. Length: About 11.8 cm. Width: About 9.3 cm. Shape: Broadly ovate. Apex: Short apiculate. Base: Narrowly attenuate. Margin: Palmately lobed, coarsely crenate to dentate; sinuses convergent and shallow to medium in depth. Texture and luster, upper surface: Moderately to densely pubescent, not rugose; moderately velvety; slightly glossy. Texture and luster, upper surface: Moderately to densely pubescent, prominent venation; moderately velvety; matte. Venation pattern: Pinnate, reticulate. Color: Developing leaves, upper surface: Close to 143A to 143B. Developing leaves, lower surface: Close to 144A. Fully developed leaves, upper surface: Close to NN137A; venation, close to 146B. Fully developed leaves, lower surface: Close to 147B; venation, close to 146C. Petioles: Length: About 2.8 cm. Diameter: About 3 mm by 4 mm. Strength: Moderately strong. Texture and luster, upper and lower surfaces. Moderately to densely pubescent; moderately glossy. Color, upper surface: Close to 147C; edges, close to 143A. Color, lower surface: Close to 146D; edges, close to 147B. Stipules: Quantity and appearance: Two leafy stipules, opposite, at the petiole attachment to the stem. Length: About 1.3 cm. Width: About 1 cm. Shape: Obovate. Apex: Short apiculate. Base: Cuneate. Texture and luster, upper surface: Moderately to densely pubescent, not rugose; moderately velvety; slightly glossy. Texture and luster, upper surface: Moderately to densely pubescent, prominent venation; moderately velvety; matte. Color: Upper surface: Close to NN137A; venation, close to 146B. Lower surface: Close to 147B; venation, close to 146C.

Inflorescence description:

*Appearance*.—Decorative inflorescence form with oblanceolate-shaped ray florets; inflorescences borne perpendicular to peduncles and face mostly upright; ray florets develop acropetally on a capitulum.

*Fragrance*.—Faintly fragrant; sweet.

*Flowering response*.—Under natural conditions, plant flower in the autumn/winter in the Northern Hemisphere; at other times of the year, inflorescence initiation and development can be induced under short day/long night conditions (at least 13.5 hours of darkness); plants exposed to two weeks of long day/short night conditions after planting followed by photoinductive short day/long night conditions flower about 70 days later when grown as a spray-type; uniform flowering habit.

*Postproduction longevity*.—Good postproduction longevity; in an interior environment, inflorescences and foliage will maintain good color and substance for about two weeks; inflorescences persistent.

*Quantity of inflorescences*.—Typically grown as a disbud type therefore, only the terminal inflorescence develops.

*Inflorescence size*.—Diameter: About 11.3 cm. Depth (height): About 7.4 cm.

*Receptacles*.—Height: About 6 mm. Diameter: About 1.5 cm. Shape: Broad inverted cordate. Color: Close to 193A and 193D.

*Inflorescence buds*.—Height: About 8 mm. Diameter: About 1.7 cm. Shape: Flattened globular. Texture and luster: Smooth and glabrous; base of immature bracts is moderately pubescent; matte. Color: Close to 137C and 138D.

*Ray florets*.—Quantity and arrangement: About 400 arranged in about ten whorls. Length: About 1.8 cm to 5.5 cm. Width: About 0.4 cm to 1.8 cm. Shape: Oblanceolate; strongly concave; moderately carinate. Apex: Bluntly acute to emarginate. Base: Attenuate. Margin: Entire; not undulate. Aspect: Initially upright to eventually horizontal. Texture and luster, upper surface: Smooth, glabrous; moderately velvety to velvety; not rugose; matte. Texture and luster, lower surface: Smooth, glabrous; moderately velvety; not rugose; slightly glossy. Color: When opening, upper and lower surfaces: Close to 155C; distally, close to between 150D and 157D. Fully opened, upper surface: Close to NN155D; venation, close to NN155D; color does not change with development. Fully opened, lower surface: Close to NN155B; venation, close to NN155B; color does not change with development.

*Disc florets*.—To date, disc floret development has not been observed on plants of the new *Chrysanthemum*.

*Involucral bracts*.—Quantity and arrangement: About 50 arranged in three whorls. Length: About 1.4 cm. Width: About 3.5 mm. Shape: Narrowly ovate. Apex: Obtuse. Base: Cuneate. Margin: Entire. Texture and luster, upper surface: Smooth, glabrous; glossy. Texture and luster, lower surface: Moderately pubescent; matte. Color, upper surface: Close to 146B to 146C; margins, translucent, and close to 157D; apices, close to N199A. Color, lower surface: Close to 137B; margins, translucent, close to 157D; apices, close to N199A.

*Peduncles*.—Length: About 6.7 cm. Diameter: About 7 mm. Strength: Strong. Aspect: Mostly upright. Texture and luster: Moderately to densely pubescent; matte. Color: Close to 147A and 147B.

*Reproductive organs*.—Androecium: Androecium development has not been observed on plants of the new *Chrysanthemum*. Gynoecium: Present on ray florets. Quantity: One per floret. Pistil length: About 6 mm. Style length: About 6 mm. Style color: Close to 150C. Stigma diameter: About 1 mm. Stigma shape: Cleft, decurrent. Stigma color: Close to 154B. Ovary color: Close to 145D.

*Seeds and fruits*.—To date, seed and fruit production have not been observed on plants of the new *Chrysanthemum*.

Pathogen & pest resistance: Plants of the new *Chrysanthemum* have been observed to be resistant to *Fusarium* Wilt (*Fusarium oxysporum f.* sp. *chrysanthemi*). To date, resistance to pests and other pathogens common to *Chrysanthemum* plants has not been observed on plants of the new *Chrysanthemum* grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFBAV1' as illustrated and described.

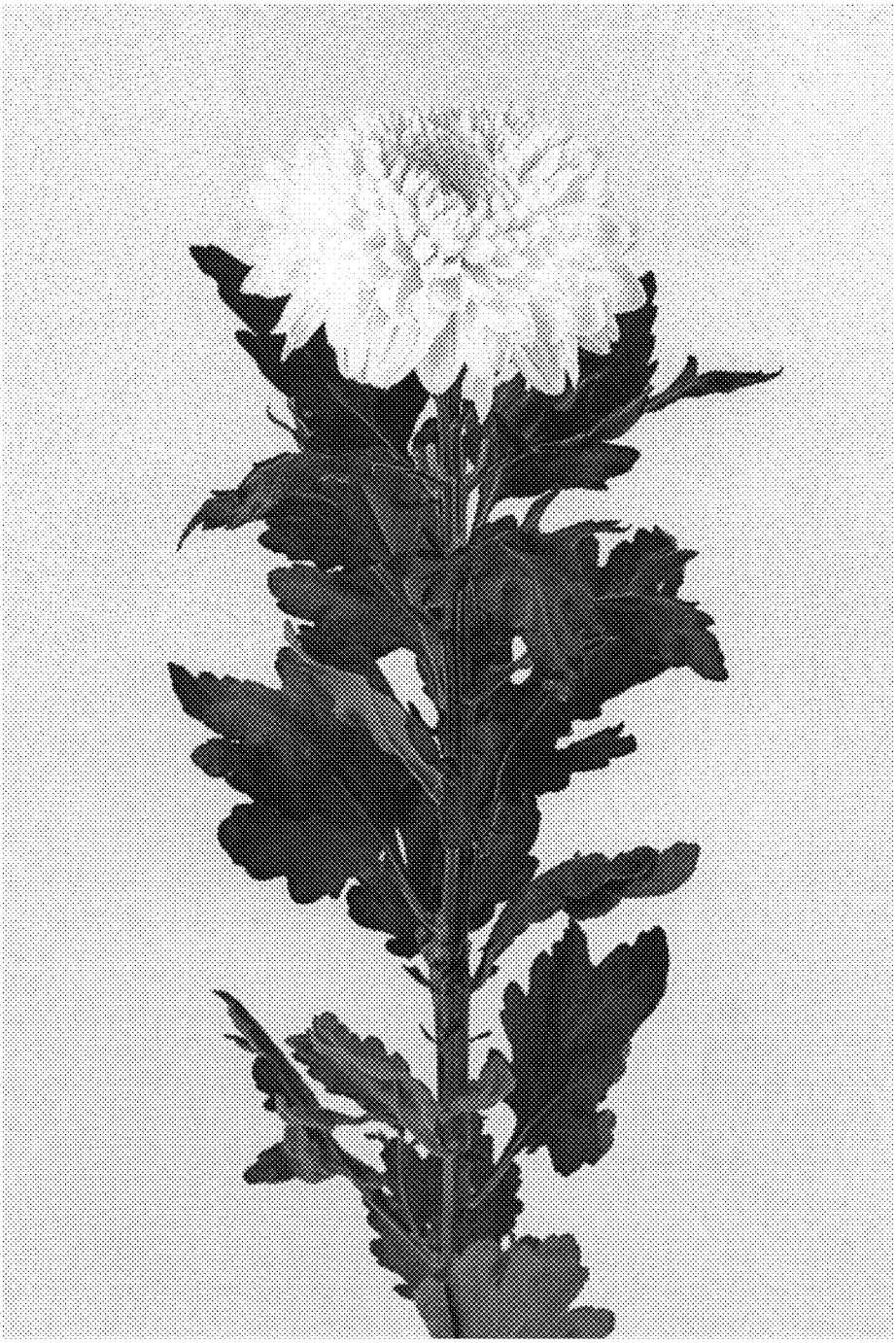

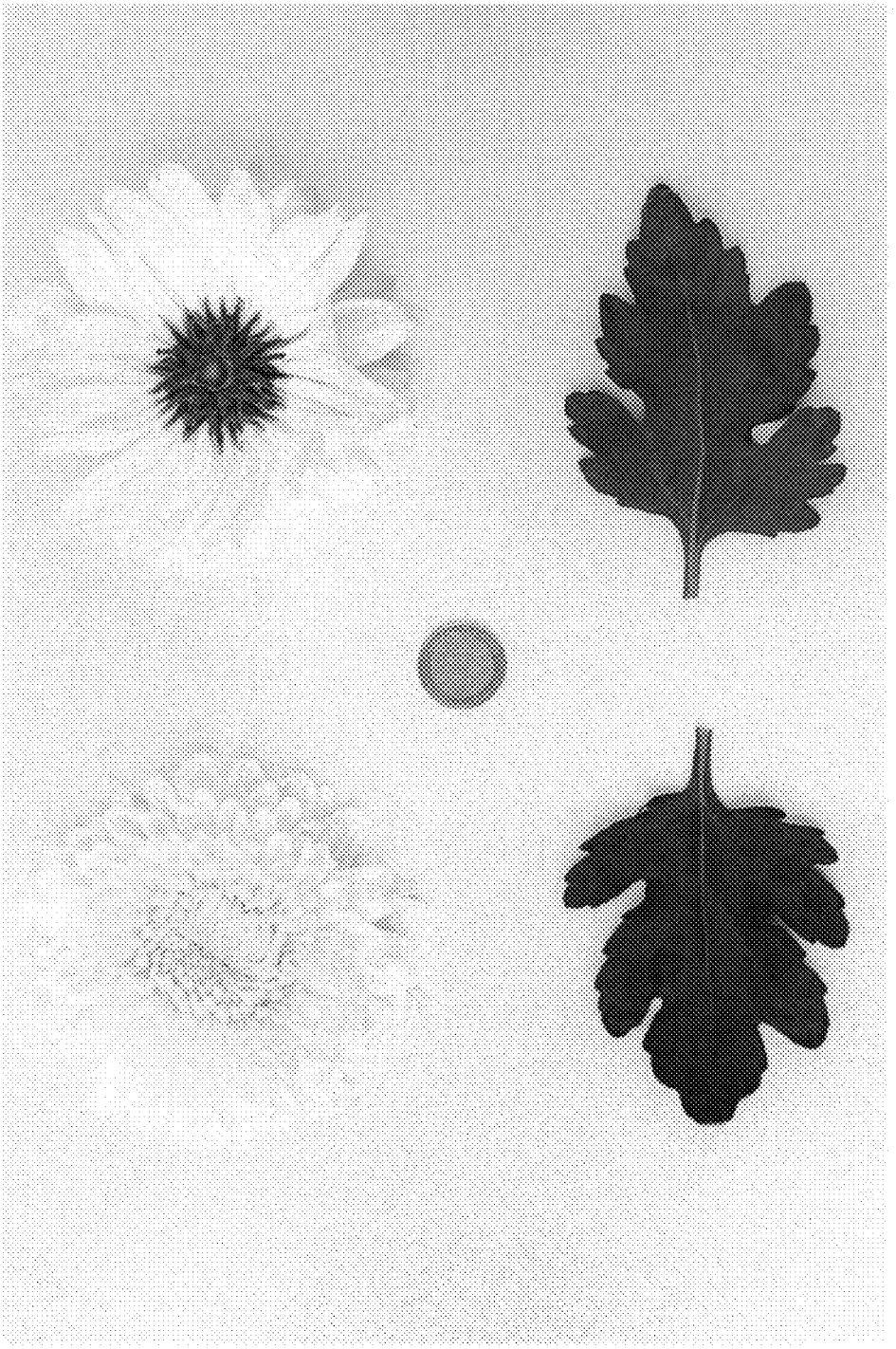

* * * * *